(12) United States Patent
Moroli

(10) Patent No.: US 9,683,944 B2
(45) Date of Patent: Jun. 20, 2017

(54) METHOD FOR THE SURFACE INSPECTION OF LONG PRODUCTS AND APPARATUS SUITABLE FOR CARRYING OUT SUCH A METHOD

(71) Applicant: CENTRO SVILUPPO MATERIALI S.P.A., Rome (IT)

(72) Inventor: Valerio Moroli, Rome (IT)

(73) Assignee: CENTRO SVILUPPO MATERIALI S.P.A., Rome (IT)

(*) Notice: Subject to any disclaimer, the term of this patent is extended or adjusted under 35 U.S.C. 154(b) by 0 days.

(21) Appl. No.: 14/892,795

(22) PCT Filed: May 23, 2013

(86) PCT No.: PCT/IT2013/000145
§ 371 (c)(1),
(2) Date: Nov. 20, 2015

(87) PCT Pub. No.: WO2014/188457
PCT Pub. Date: Nov. 27, 2014

(65) Prior Publication Data
US 2016/0103079 A1    Apr. 14, 2016

(51) Int. Cl.
*G01N 21/00* (2006.01)
*G01N 21/89* (2006.01)
G01N 21/952 (2006.01)
G01N 21/88 (2006.01)

(52) U.S. Cl.
CPC ..... *G01N 21/8903* (2013.01); *G01N 21/8806* (2013.01); *G01N 21/8901* (2013.01); *G01N 21/952* (2013.01); *G01N 2021/8845* (2013.01)

(58) Field of Classification Search
CPC .. G01N 21/956; G01N 21/94; G01N 21/8806; G01N 21/95607; G01N 21/9501
USPC ............................................... 356/237.2
See application file for complete search history.

(56) References Cited

U.S. PATENT DOCUMENTS

| | | | |
|---|---|---|---|
| 4,358,202 A | 11/1982 | Puffer et al. | |
| 6,191,856 B1 | 2/2001 | Slemon et al. | |
| 6,598,994 B1 | 7/2003 | Tait et al. | |
| 6,859,285 B1 | 2/2005 | Chang | |
| 6,950,546 B2 | 9/2005 | Chang et al. | |
| 2002/0008203 A1 | 1/2002 | Chang | |
| 2003/0169418 A1 | 9/2003 | Fujii et al. | |
| 2004/0105001 A1* | 6/2004 | Chang ............... | G01N 21/952 348/92 |

(Continued)

FOREIGN PATENT DOCUMENTS

| | | |
|---|---|---|
| EP | 1582068 A2 | 10/2005 |
| FR | 2873207 A1 | 1/2006 |

OTHER PUBLICATIONS

International Search Report and Written Opinion based on International Application No. PCT/IT2013/000145 mailed Mar. 14, 2014. (12 Pages).

*Primary Examiner* — Tarifur Chowdhury
*Assistant Examiner* — Md M Rahman
(74) *Attorney, Agent, or Firm* — Lucas & Mercanti, LLP

(57) ABSTRACT

Disclosed are a method and apparatus for the surface inspection and detection of defects of long products by means of a combination of images of the same region of the long product. The images are taken under different lighting condition in order to reconstruct the shape of the surface and thus obtain information on the presence of defects.

8 Claims, 12 Drawing Sheets

(56) References Cited

U.S. PATENT DOCUMENTS

2005/0276441 A1\* 12/2005 Debevec ................ H04N 5/222
  382/100
2006/0000989 A1   1/2006 Kuriyama et al.
2015/0002847 A1\* 1/2015 Sukegawa .............. G01B 11/24
  356/445

\* cited by examiner

METHOD FOR THE SURFACE INSPECTION OF LONG PRODUCTS AND APPARATUS SUITABLE FOR CARRYING OUT SUCH A METHOD

CROSS-REFERENCE TO RELATED APPLICATIONS

This application is a 371 of PCT/IT2013/000145, filed May 23, 2013.

FIELD OF THE INVENTION

The invention refers to the field of the methods for surface defect detection of long product during working thereof.

BACKGROUND OF THE INVENTION

The object of the present invention is a method for surface optical inspection of long products in production or working plants, also at high temperature.

By an exemplary way the inspected product can be a bloom, a slab, a billet, a bar, a wire rod, a wire, a sheet, a tape, or a beam, obtained by rolling, drawing, grinding and other methods commonly used in continuous or batch production, consisting of any material like steel, metallic alloys, plastic, ceramics, wood, paper or other.

As it is known, the presence or absence of surface defects is a major criterion in order to estimate the quality of long products and in order to prevent the refusal or replacement demand of defective products by purchasers.

Therefore various systems in order to resolve the problem of surface inspection of long products and detection of related surface defects have been suggested. Some used systems are described in U.S. Pat. No. 6,859,285 B1, US 2002/0008203 A1 and EP 1 582 068 B1.

In U.S. Pat. No. 6,950,546 B2, said problem, for example, has been resolved using a system comprising: a plurality of illuminators disposed around the long product, each one projecting light with a set angle with respect to line perpendicular to lightened surface; a plurality of image detectors, disposed around the long product, having main axis inclined with respect to said line with a second set angle; and a computerized unit for acquisition and processing of said images.

The sensitivity of these systems and ability thereof to measure both small and wide angles of occurring discontinuities are not however completely satisfactory.

In FR2873207A1 a device the use thereof seems to involve a method in order to inspect the surface and detect defects of long products during working consisting of the following steps is described:

illuminating an annular portion of surface of the long product with a plurality of illuminators each one projecting light with a set angle with respect to line perpendicular to lightened surface;

detecting reflexed images by a plurality of detectors having main axis inclined with respect to said line with a second set angle;

acquiring and processing said images by means of a computerized unit; and using a combination of images of the same region of the long product, said images being taken under different lighting conditions, in order to rebuilt shape of surface and thus obtaining information about the presence of defects.

However in the specific field the need to have of a system resulting in improved detection sensitivity and flexibility exists.

SUMMARY

Said need is satisfied by the method according to the present invention that offers other advantages as it will be apparent as below reported.

Accordingly it is an object of the present invention a method to inspect the surface and detect defects of long products during working thereof, said method comprising the steps of:

lighting an annular portion of the long product surface by a plurality of illuminators, each one projecting light with a set angle with respect to line perpendicular to lightened surface;

detecting reflexed images by a plurality of detectors having their main axis inclined with respect to said line with a second set angle;

acquiring and processing said images by a computerized unit;

using a combination of images of the same region of the long product, said images being taken under different lighting conditions, in order to rebuilt shape of surface and thus obtaining information about presence of defects, wherein point defects generating an angle along the product advancing direction are made evident using an assembly of cameras which are transverse with respect to the product, and two or more lighting groups, some of which are provided before, and others after, said cameras, and wherein defects are individuated comparing images obtained for the same product region under the different lighting conditions, shooting of the same region with different lighting conditions being taken at the same time exploiting color cameras and using illuminators with different wavelengths.

BRIEF DESCRIPTION OF THE DRAWINGS

The description of the present invention will be carried out with reference to enclosed drawings whose meaning is as below.

DETAILED DESCRIPTION

The method according to the invention uses optical techniques aiming to determine the shape of the product surface, in order to detect discontinuities that can constitute a defect in the production cycle.

The used optical techniques are based on the employment of more shootings of the same region of the material under various lighting conditions, in order to determine not only the visual appearance of the material, but also the shape of surface thereof.

Given the nature of the product, i.e. developed substantially along a main direction (working direction), the method of the invention uses in particular two embodiments for the determination of the surface shape (named below also like "variant" or "modality").

Figure 1:
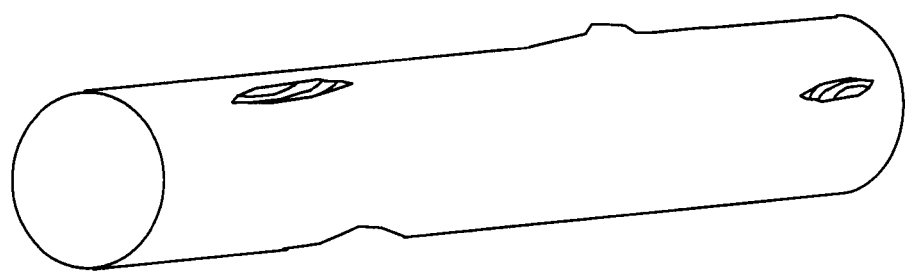
FIG. 1 shows an example of point defects on the surface of a product.

The first modality is aimed to characterize longitudinal discontinuities along the main development of the same product. These can be, for example small nicks, burring, impressions, material inclusions, or other small size defect creating discontinuity on the surface of the material along the working direction (FIG. 1).

Figure 2:
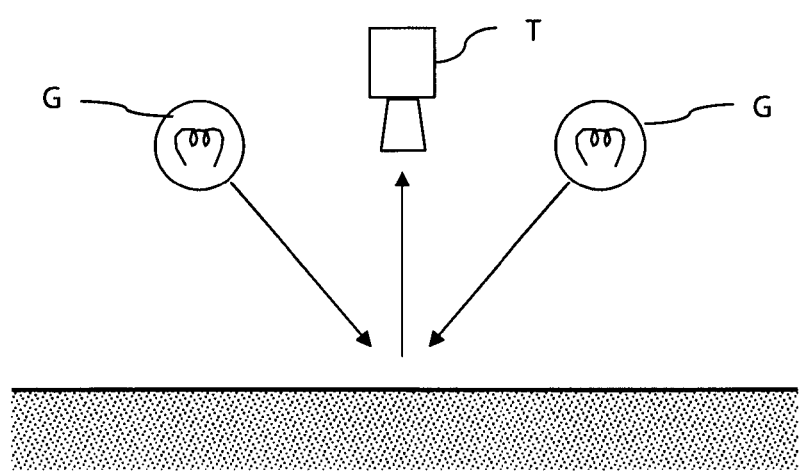
FIG. 2 shows an embodiment for shooting of point defects.

In order this type of discontinuity to be detected, below referred as point defects, cameras T which are transverse with respect to the product, and two lighting groups G, one of which is provided before, and another after (FIG. 2) are used. The graphical representations used in this figure for the lighting groups G and cameras T are used also in the majority of successive figures.

Figure 3:
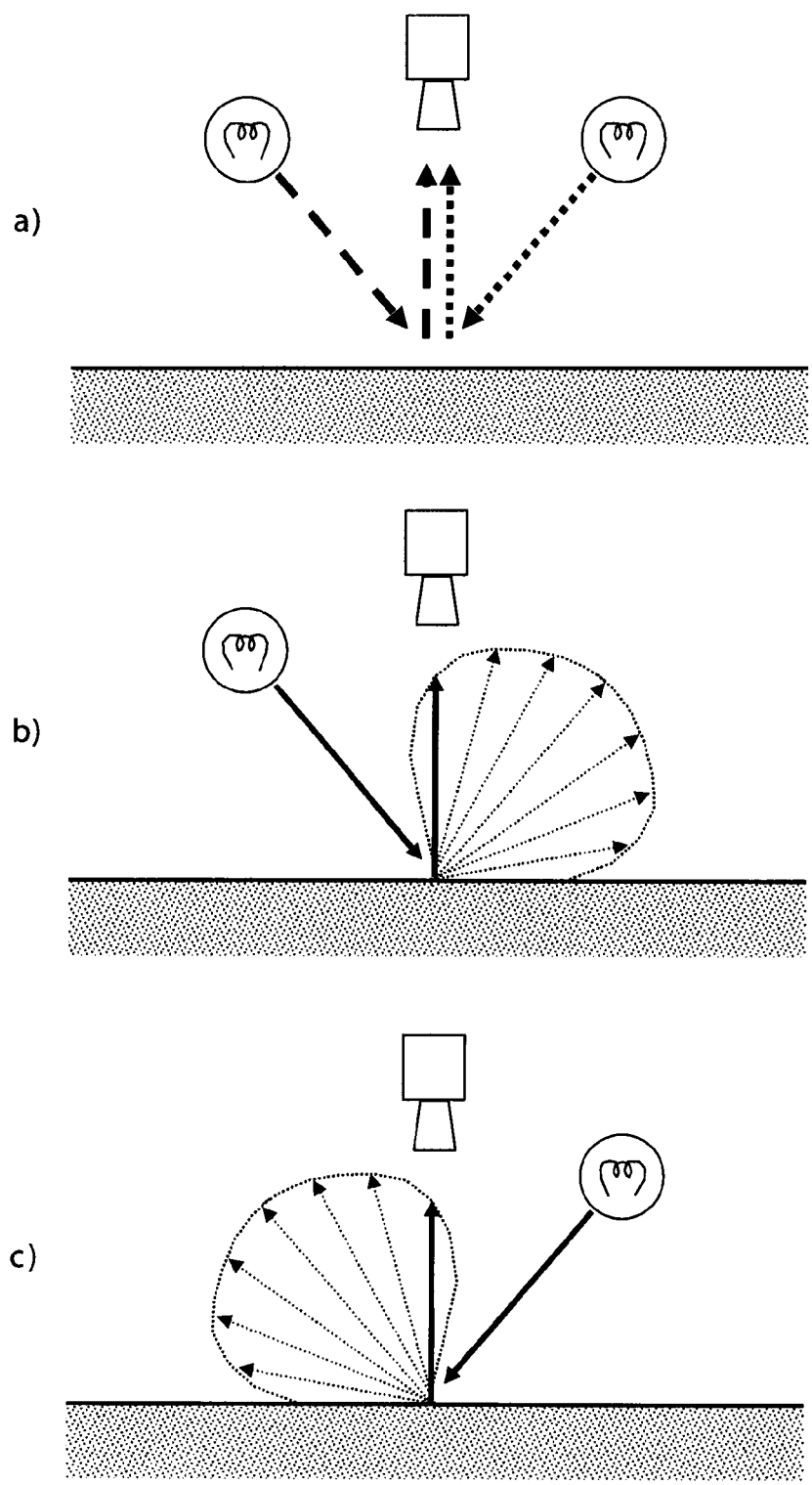
FIG. 3 shows the behaviour of the system in absence of point defects.

Under normal conditions, if the product surface does not display point defects, acquired signals for each material region corresponding to said two lighting conditions is the same (FIG. 3a). In fact the perceived light radiation from the camera comes from scattering of the incident radiation; irrespective of the form of scattering diagram, the radiation scattered under two lighting conditions is the same one, if the two sources are symmetrical with respect to the camera (FIG. 3b and FIG. 3c).

Figure 4:
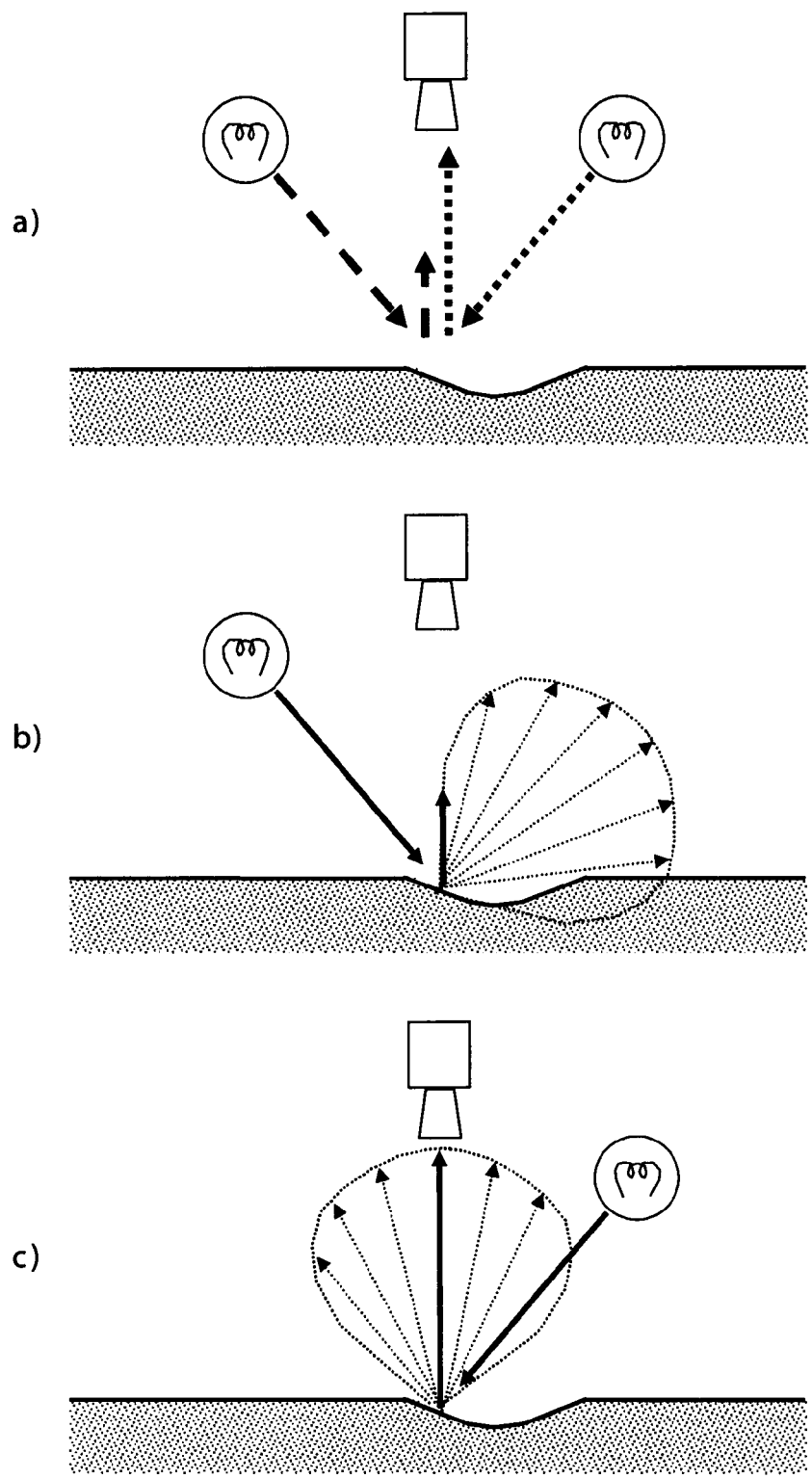
FIG. 4 shows the behaviour of the system in presence of point defects.

When a point defect occurs in sight to the system, instead, there are necessarily defect surface sections displaying inclination different than normal one (FIG. 4a). The inclination of these regions modifies the behaviour of the diffusion phenomenon on the same surface, favouring the scattering of light from the lighting group being closer to the reflection condition (FIG. 4b), and disadvantaging the scattering for the other group (FIG. 4c).

Figure 5:
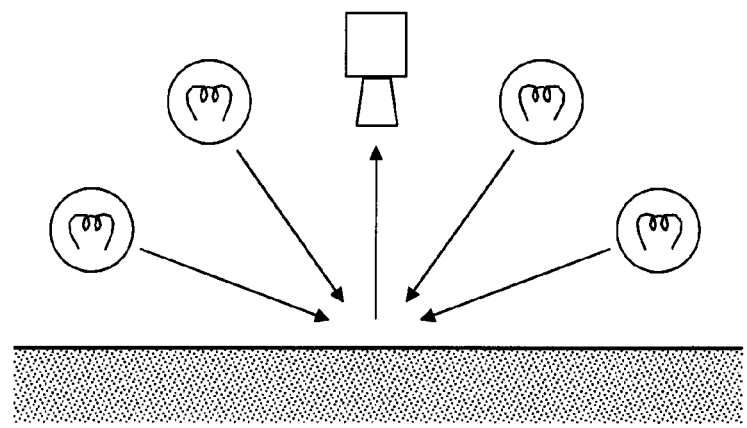
FIG. 5 shows another embodiment for shooting of point defects.

Generally more than two lighting groups can be used, some placed before and others after the cameras, in order to improve the system sensitivity and ability thereof to measure both small and large angles of the discontinuities occurring on the surface (FIG. 5). Moreover the use of more than one lighting groups placed at various angles allows the system behaviour to be modulated according to materials or surface finishes resulting in differently wide scattering shapes.

Figure 6:
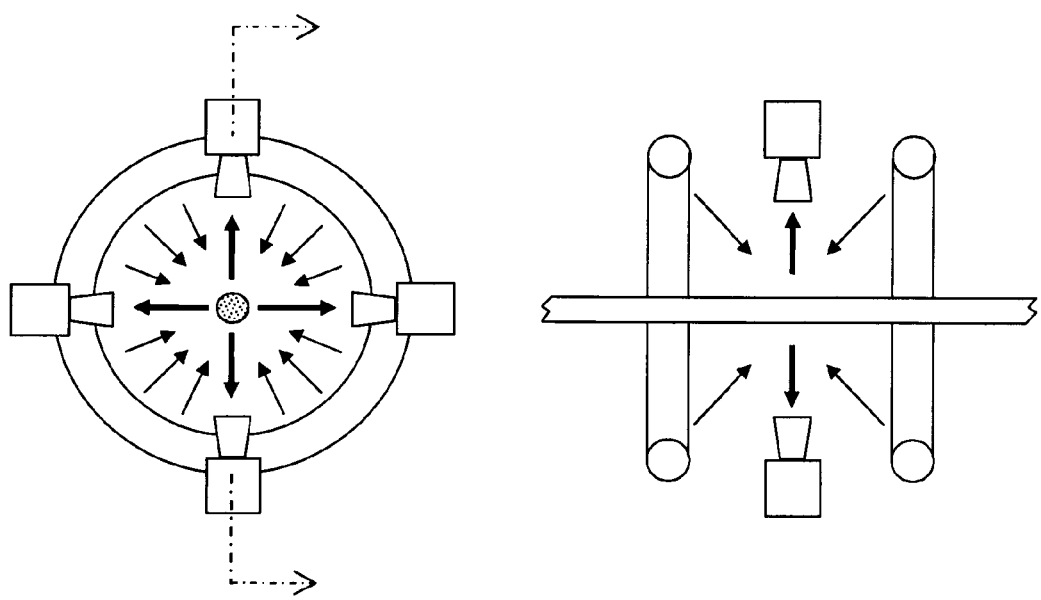
FIG. 6 shows an embodiment for shooting of point defects on materials with circular or almost circular shape.
Figure 7:
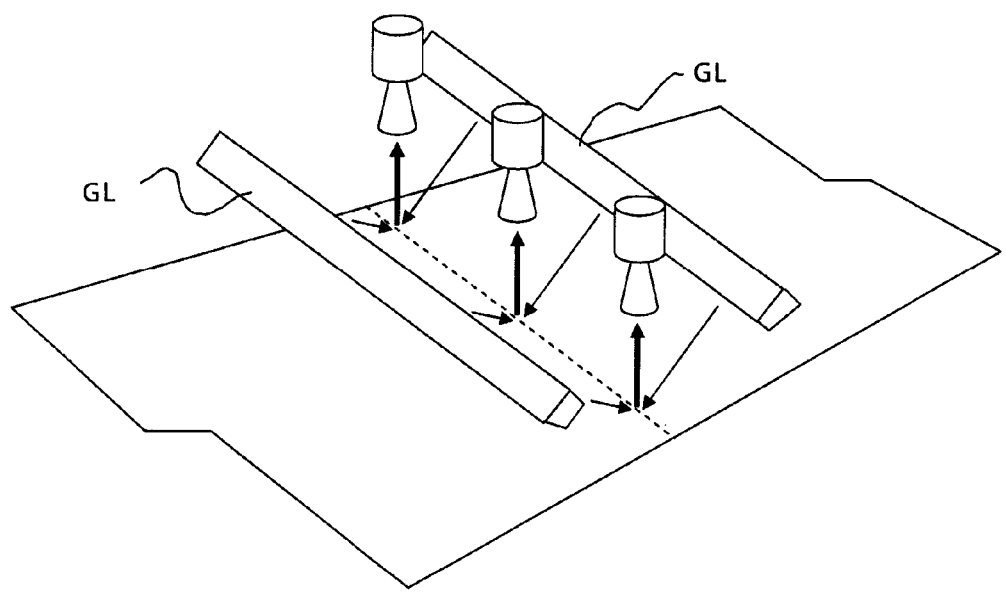
FIG. 7 shows an embodiment for shooting of point defects on materials with of flat shape.

The number of usable cameras, type thereof and disposition of the lighting groups can be variable depending on the geometry and nature of the product. By an exemplification, for example for cylindrical circular or almost circular cross-section shaped products 4 or more linear cameras, and two or more annular lighting groups can be used (FIG. 6). For almost flat shaped products, on the contrary, two or more linearly disposed cameras and linear lighting groups GL can be used (FIG. 7), being possible in general terms the inspection of the edges of the tape to be omitted. In general terms the use of linear cameras allows the holding of an uniform lighting and shooting condition along all the image, that is acquired taking advantage of the material advancing movement through the system.

In order to obtain the contemporary shooting of the material under various lighting conditions various techniques can be used. According to an embodiment the system can use colour cameras and lighting groups at different wavelengths. This format allows to obtain images wherein single colour channels (for example RGB, i.e. Red, Green, Blue) are obtained at the same time, and everyone is produced by the single lighting originating from correspondent wavelength illuminators. According to another variant, the almost contemporary shooting of the same region under different lighting conditions is obtained switching on in sequential way at high speed the lighting groups and opportunely synchronizing the cameras, subdividing then the shootings of the cameras in images corresponding to each lighting condition, in order to reconstruct images obtained from the single switching on of everyone of the illuminators.

Figure 8:
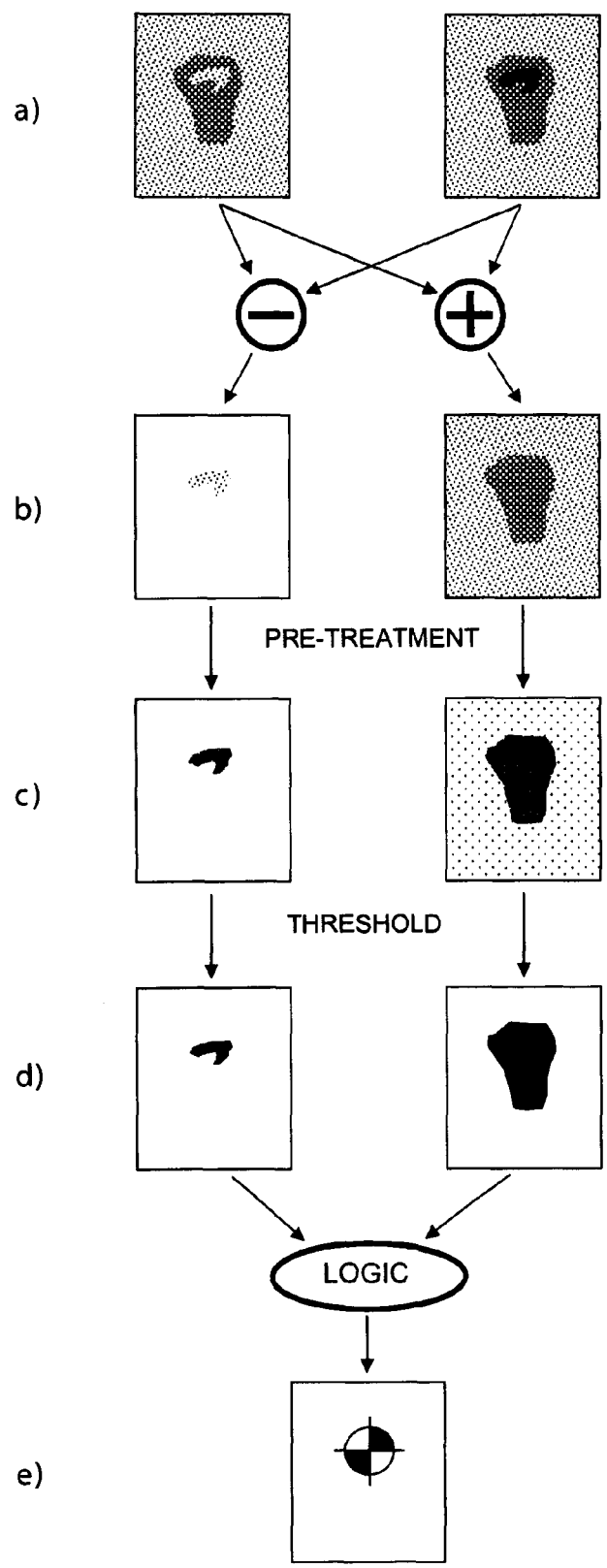
FIG. 8 shows a technique for processing of camera acquired images aiming to characterize point defects.

It is possible to employ various techniques allowing to use acquired images in order to determine the discontinuity presence and therefore to signal the possible presence of point defects. For example according to an embodiment it is possible to carry out the comparison of the images obtained for the same region of the product under two different lighting conditions (FIG. 8a) thus generating two new images obtained by summing and subtracting the two original images (FIG. 8b). Successively it is possible to use digital filters for the pre-processing of the two obtained images (FIG. 8c), and therefore to determine the areas of the two images displaying brightness outside fixed limits (FIG. 8d). At last, the areas determined in the preceding step can be combined to each other using logic rules that afford to detect the defective regions (FIG. 8e).

Figure 9:
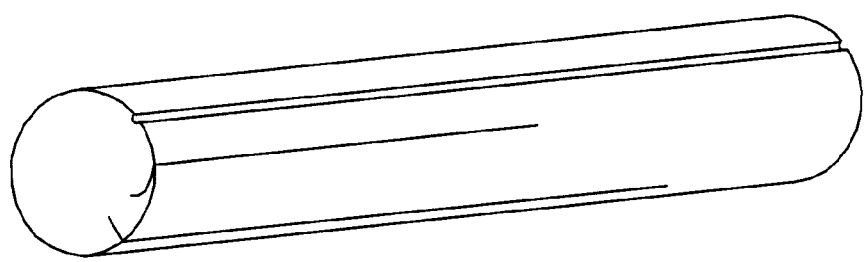
FIG. 9 shows an example of long defects on the surface of a product.

The second inspection modality instead is aimed to detect defects that do not induce substantial longitudinal discontinuities along the main development of the same product. These can be for example threading, fractures or cracks, material folding, or other defect having a continuous development on the material along the working direction (FIG. 9).

Figure 10:
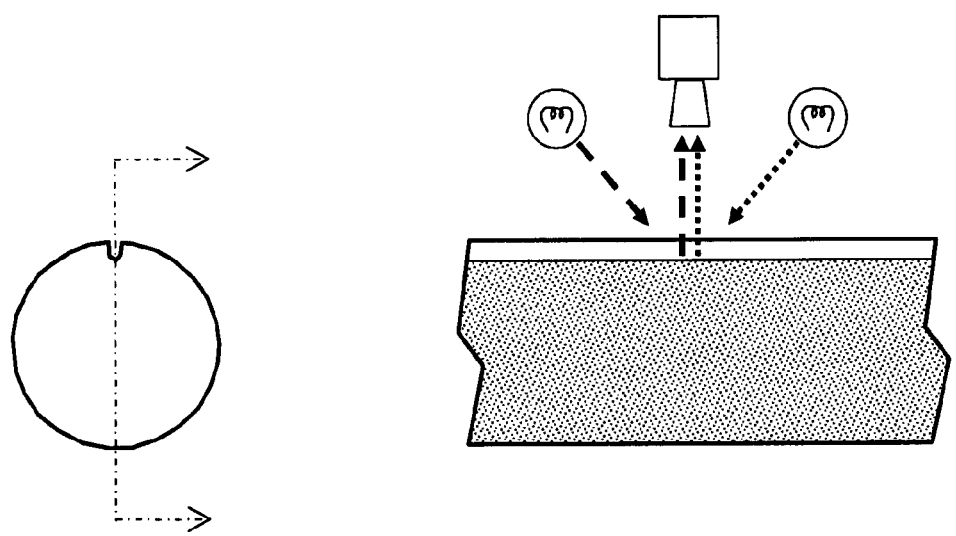
FIG. 10 shows the behaviour of long defect if shot according to the method suitable to point defect shooting.

The presence of these defects, below referred as long defects, on the contrary with respect to previously illustrated circumstance does not induce an inclination of the surface along the working direction (FIG. 10). On the contrary, instead, these defects are characterized in that the same generate an anomalous inclination along the perimeter of the product cross-section perpendicular to the advancing direction.

Figure 11:
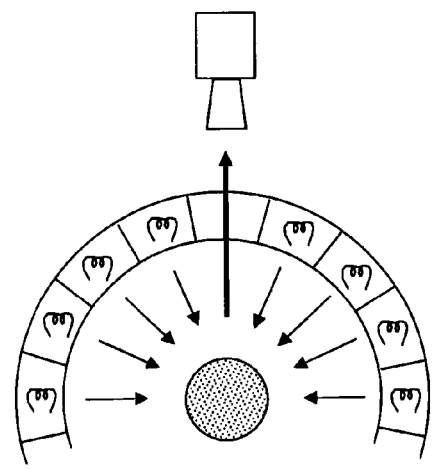
FIGS. 11 to 13 show an embodiment for shooting of long defects.

Therefore, for the detection of this discontinuity type cameras transverse to the same product and one or more illuminators surrounding the inspection cross-section and consisting of distinguished sections are used (FIG. 11).

Figure 12:
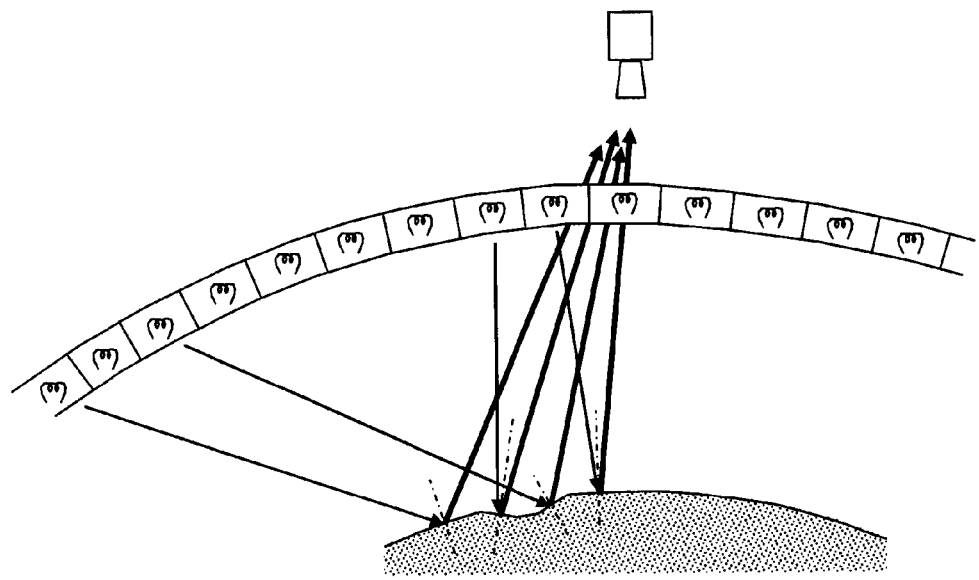

By acquiring the images of the product in correspondence to switching on the various sections of the illuminators, it is possible to detect the inclination of every portion of the surface, considering that the signal perceived by the camera is maximum in correspondence to the lighting condition being more specular to the camera compared to the inclination of surface (FIG. 12).

Figure 13:
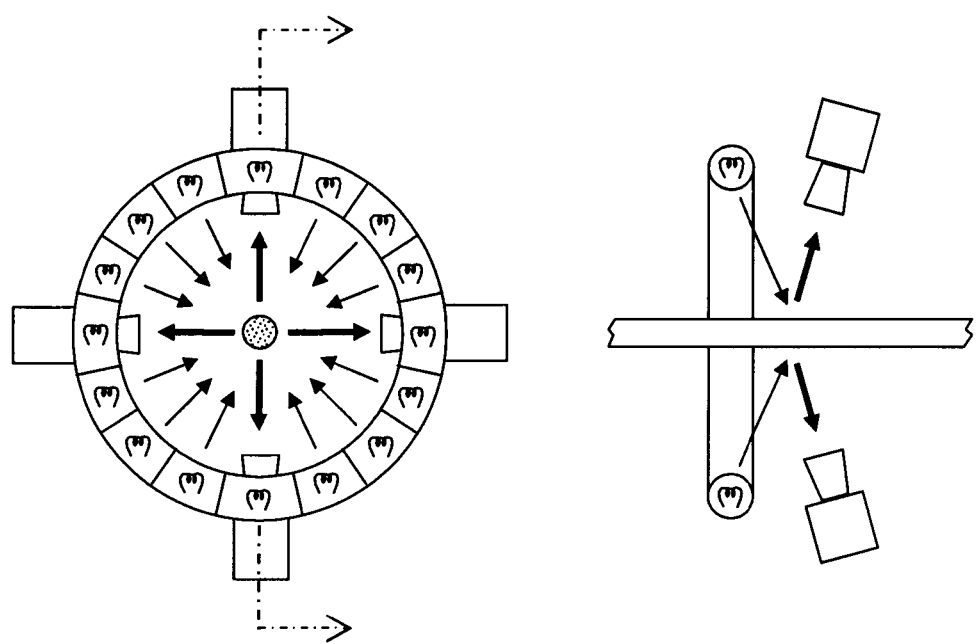

The number of usable cameras, type thereof and the disposition of the lighting groups also in this case can vary according to geometry and nature of the product. For example, as an exemplification for cylindrical circular cross-section products 4 or more linear cameras, and one or more annular lighting groups consisting of individually addressable can be used (FIG. 13).

Analogously to the description for inspection modality aimed to the detection of longitudinal discontinuities, also for the inspection of the long defects it is possible to use various techniques for the contemporary shooting of the material under various lighting conditions. In particular, as already described, colour cameras and illuminator groups at different wavelengths can be used, or it is possible to switch on in sequential way at high speed the lighting groups opportunely synchronizing the cameras.

Figure 14:
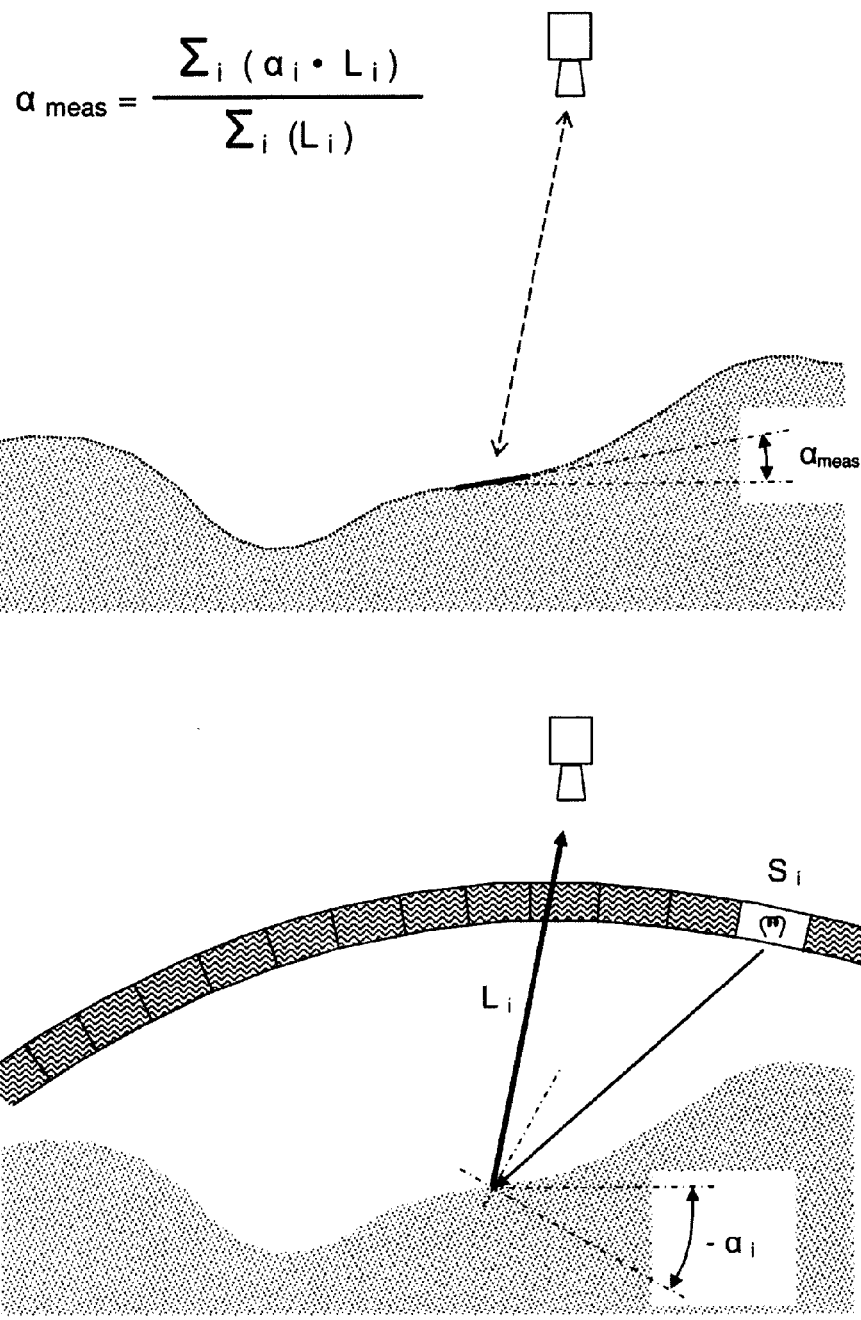
FIG. 14 shows a technique for processing the camera acquired images aiming to characterize long defects.

Also for the detection of the long defects various techniques allowing to use the acquired images aiming to determine the discontinuity presence and therefore to signal the possible presence of defects can be implemented. For example according to another embodiment (FIG. 14) it is possible to use the images obtained by switching on the single illuminator groups, by measuring the angle of the surface of a point ($\alpha_{meas}$) carrying out for that point a weighted average of the angles ($\alpha_i$) of the surface that would maximize the response to light coming from switched on illuminator groups ($S_i$), weighing said average with the intensity ($L_i$) measured in correspondence of each configuration of illuminator switching on.

The two illustrated inspection modalities, that is the first aimed to the detection of point defects and the second aimed to the detection of long defects, can be usefully combined to each other implementing a method/apparatus for the inspection suitable to recognize various types of defects. This can be carried out simply by coupling the two systems, each equipped with own cameras and illuminators or also using common items for the two systems, with simplification advantage and reduction of device complexity.

Figure 15:
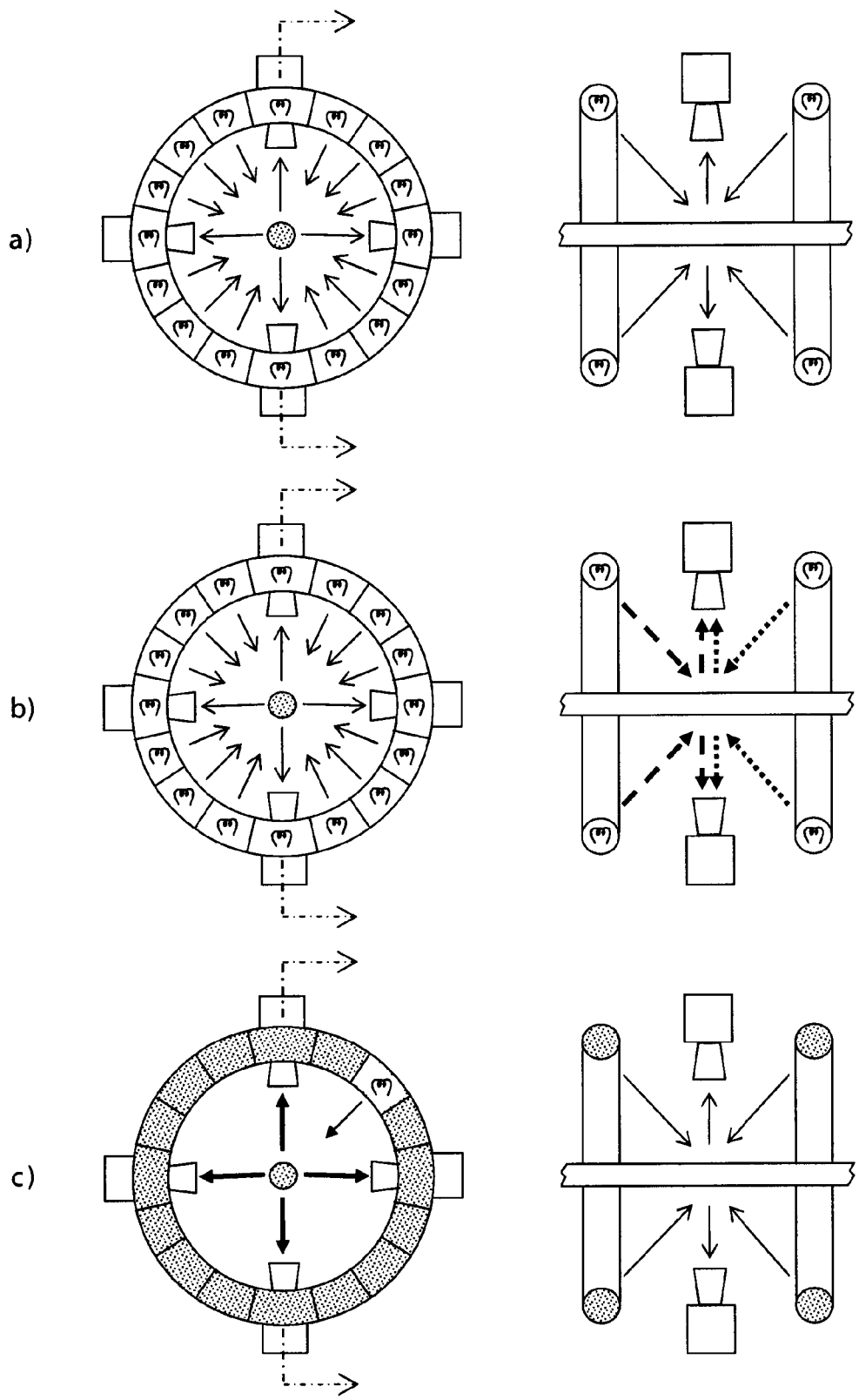
FIG. 15 shows in schematic way a variant of the invention for the inspection and recognizing of point defects and long defects.

For this purpose it is useful to consider that the long defects e.g. (lines, crack or fractures, folding) normally interest a remarkable length of the product along the working direction. Therefore, the control of the presence of said defects can be carried out also in not continuous way, freeing the cameras and the illuminators and making available thus for the majority of the time to the search of point defects. The system therefore can use two lighting groups, for example consisting of individually usable groups, said two groups being located upstream and downstream of cameras, respectively (FIG. 15a). During the majority of the time said illuminators are used according to the first described operating modality, aiming to the detection of point defects, observing the intensity difference of radiation coming from the two lighting groups (FIG. 15b). When, for example, colour cameras are used, the two lighting groups can have two different wavelengths and maintained completely switched on during such step.

At regular intervals, the system can switch to the operating modality aiming to the detection of the long defects. This step for example can be implemented using the technique of switching on in sequence of illuminator groups, synchronizing the cameras in order to collect images in correspondence to the switching on of every illuminator sector (FIG. 15c). According to this operating modality the step of inspection of long defects can be carried out in very short times, using a number of lighting groups not particularly high, with the advantage that not too much time is subtracted to the process of inspection of the point defects.

The described method is suitable to be used also with materials at high temperature, both because it is possible to use illuminators and cameras operating at wavelengths wherein own irradiation of the warm material is in some extent reduced (green-blue-ultraviolet), and also because the described methods are based on acquired image comparison under various lighting conditions and therefore it is simple to understand that a possible background radiation originating from the incandescence of the material is automatically removed during the processing step.

It is an object of the present invention a method for inspection of long products using a combination of images of the same region of the product, opportunely taken under various lighting conditions, in order to reconstruct the shape of the surface and therefore to obtain information on the presence of defects.

According to a first embodiment of the method, the point defects generating an angle along the direction of product advancing movement are detected using cameras disposed transverse to the product and two or more lighting groups some being before and others after said cameras, and wherein the defects are detected comparing the images obtained in the same region of the product under different lighting conditions.

The contemporary shooting of the same region under the various lighting conditions is obtained taking advantage of colour cameras and using illuminators at different wavelengths.

Alternatively the almost contemporary shooting of the same region under various lighting conditions is obtained by switching on in sequential way at high speed the lighting groups and opportunely synchronizing the cameras, subdividing then the shootings of the cameras in images corresponding to each lighting condition, in order to reconstruct images obtained from the single switching on of everyone of the illuminators.

Two lighting groups, one placed before and the other after the cameras are used, and the comparison of the images obtained in the same region of the product under the two different lighting conditions is carried out thus generating two new images obtained by summing and subtracting the two original images, using digital filters for the pre-processing of the two obtained images, then detecting the areas of the two images displaying brightness outside fixed limits and then using logic composition rules of the regions evidenced in the sum and difference images, respectively.

According to a second embodiment of the method, the long defects, generating an angle along the perimeter of the product cross-section perpendicular to the advancing direction are detected using one or more cameras placed transverse to the product, and one or more illuminators surrounding the inspection cross-section and consisting of distinguished groups and the defects are detected by carrying out comparison of the images obtained in the same region of the product when the same is illuminated by various combinations of the illuminator sectors.

Also according to the second embodiment the contemporary shooting of the same region under various lighting conditions is obtained taking advantage of one or more colour cameras and using illuminator sectors at different wavelengths.

Alternatively, the almost contemporary shooting of the same region under various lighting conditions is obtained by switching on in sequence at high speed illuminators sectors and opportunely synchronizing the cameras, then subdividing the shootings of the cameras in images correspondents to each lighting condition.

The images obtained in the same region of the product under different lighting conditions are used in order to reconstruct the inclination of each portion of the perimeter of the product cross-section perpendicular to the advancing movement, calculating for the every point the local angle as weighted average of the angles of the surface that would maximize the response to light coming from switched on illuminator sectors, weighing said average with the intensity measured in correspondence of each configuration of illuminator switching on.

According to a third embodiment of the method according to the invention, the lighting and shooting systems are opportunely shared and allow to implement usefully both the inspection method for point defects generating an angle along the direction of product advancing movement, and also the method for the long defects generating an angle along the perimeter of the product cross-section perpendicular to the running direction, using different wavelengths or switching on at various times of the single illuminator sectors.

Generally the inspection of products at high temperature is possible employing illuminators and cameras operating at wavelengths wherein the own radiation of the hot material is somewhat reduced (green-blue-ultraviolet), and wherein a possible background radiation originating from the incandescence of the material is automatically removed during the processing step.

The present invention includes also an apparatus suitable to embody the method as above described.

Accordingly a further object of the present invention is an apparatus for identifying surface defects of a long product while it is subjected to working, according to the above described method, said apparatus comprising the following parts:

a plurality of illuminators, provided along the long product, each one projecting light according to a set angle with respect to line perpendicular to the lightened surface portion;

a plurality of detectors, provided about the long product, with relevant main axis inclined with respect to said line according to another set angle, and a computerized unit for acquiring and processing said images, characterized in that lighting groups, emitting not only white light but also light dedicated to a set wavelength, are provided in such a way to lighten according to different angles subsequent surface regions of long product, and are possibly singularly piloted to realize sequences of lighting conditions, and in that the computerized unit for acquisition and processing of said images, to provide useful indications for recognizing surface defects on the basis of shape or luminous intensity variations, uses comparison between images obtained under different lighting conditions of the product A general description of the invention has been reported up to now. By means of the examples referring to FIGS. 16 and 17 now a more detailed description of some embodiments thereof will be reported aiming to explain objectives, characteristics, advantages and operating modalities in a more fully way.

Example 1

Figure 16:
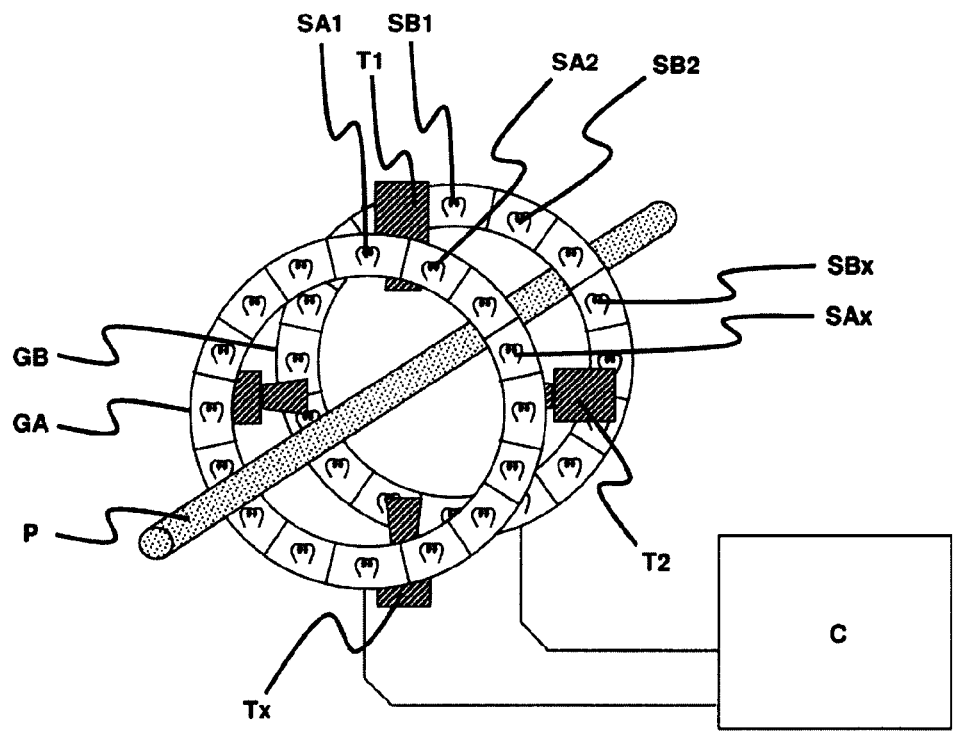
FIGS. 16 and 17 illustrate in more complete way two different embodiments of the invention.

According to a complete embodiment, as depicted in FIG. 16, the system can be provided with two lighting groups GA and GB, placed upstream and downstream of the cameras, respectively. Each of two groups emits light at different wavelength. Said groups in addition consist of SA1, SA2, SAx and SB1, SB2, SBx individually addressable sectors. The system collects the images of the product using linear colour cameras T1, T2, Tx, placed perpendicular to the surface of the product and between the two lighting groups.

The control system C checks the illuminators, maintaining all operating during the phase of search of the point defects. In this phase the point defects are detected comparing the images acquired by the system in the same regions of the product P to be inspected and analyzing the colour differences resulting from one of the two lighting groups with the detriment of the other causing a consequent chromatic change in the received radiation. In the phase of search of the long defects, on the contrary, the control system operates on the illuminators by switching on in sequence the two correspondents sectors of both groups (SA1 with SB1, SA2 with SB2, Sax with SBx . . . ). In this way the system can determine the presence of a long defect using the intensities collected in correspondence of each lighting condition, calculating for the every point the local angle as weighted average of the angles of the surface that would maximize the response to light coming from switched on illuminator sectors, weighing said average with the intensity measured in correspondence of each configuration of illuminator switching on.

Example 2

Figure 17:
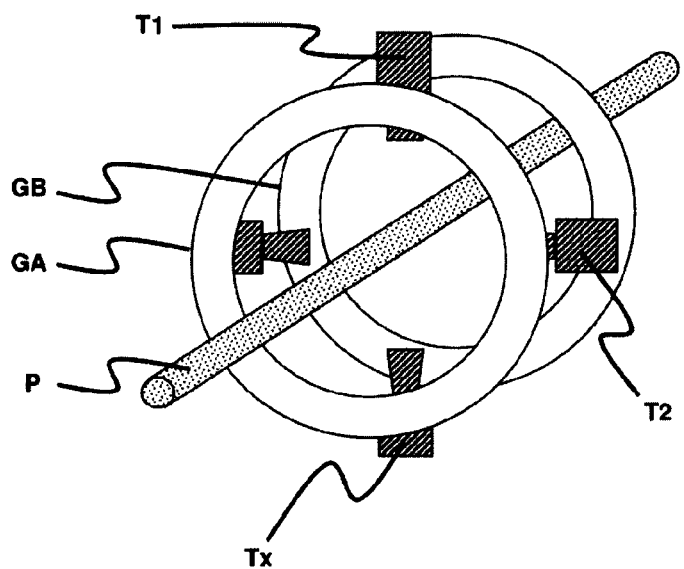

In another simpler embodiment, as illustrated in FIG. 17, the system can be equipped with two lighting groups GA and GB, placed upstream and downstream of the cameras, respectively. Each of said two groups emits at different wavelength. The system collects the images of the product using a set of linear colour cameras i.e. T1, T2, Tx, placed perpendicular to the surface of the product and between the two lighting groups. The point defects are detected comparing the images collected from the system in the same regions of the product P to be inspected and analyzing the colour differences resulting from the fact that the same point defects induce the increase of the radiation perceived from one of the two lighting groups with the detriment of the other causing a consequent chromatic change in the received radiation.

The invention claimed is:

1. A method for inspecting surface and detecting defects of long products while they are subjected to working, comprising:

lighting an annular portion of the long product surface by a plurality of illuminators, each one projecting light with a set angle with respect to line perpendicular to lightened surface;

detecting reflexed images by a plurality of detectors having their main axis inclined with respect to said line with a second set angle;

acquiring and processing said images by a computerized unit;

using a combination of images of the same region of the long product, said images being taken under different lighting conditions, in order to rebuilt shape of surface and thus obtaining information about presence of defects, wherein point defects generating an angle along the product running direction are made evident using an assembly of cameras which are transverse with respect to the product, and two or more lighting groups, some of which are provided before, and others after said cameras, and wherein defects are individuated comparing images obtained for the same product region under the different lighting conditions, shooting of the same region with different lighting conditions being taken at the same time exploiting color cameras and using illuminators with different wavelengths; and wherein long defects, generating inclination along perimeter of product section perpendicular with respect to running direction are made evident using one or more than one cameras provided transversely with respect to the product, and one or more than one illuminators surrounding inspection section and that are comprised of different sectors, and wherein defects are individuated by making a comparison of images obtained in the same region of the product when the latter is lightened by different combination of illuminators sectors.

2. The method as claimed in claim 1, wherein almost contemporaneous shooting of the same region with different lighting conditions is obtained switching on in sequence and at a high speed lighting groups and suitably synchronizing cameras and then subdividing the shootings of the cameras in images correspondents to each lighting condition in order to reconstruct images obtained by switching on each single illuminator.

3. The method as claimed in claim 1, wherein two lighting groups are used, one placed before said cameras and the other one placed after said cameras, and wherein comparison of images obtained in the same region of the product with two different lighting conditions is carried out by generating two new images obtained by summing and subtracting the two original images, using digital filters for the pre-processing of the two obtained images thus detecting areas of two images having luminosity beyond set limit values, and thus employing logic composition rules of evidenced regions in sum image and in difference image.

4. The method as claimed in claim 1, wherein contemporaneous shooting of the same region with different lighting conditions is obtained by exploiting one or more color cameras and using sectors of illuminators having different wavelengths, or wherein almost contemporaneous shooting of the same region with different lighting conditions is obtained switching on in sequence and at a high speed illuminator sectors and suitably synchronizing cameras, then dividing cameras shooting into images corresponding to each lighting condition.

5. The method as claimed in claim 4, wherein images obtained in the same product region with different lighting conditions are used to reconstruct angle of each part of perimeter of product section perpendicular to running, calculating for each point local angle as weighted average of surface angles that would have made maximum response to light arriving from switched on illuminators sectors, weighting said average with intensity measured in correspondence of each illuminator switching on configuration.

6. The method of claim 1, wherein lighting and shooting systems are suitably shared and permit usefully implementing either inspection method for point defects generating an angle along product running direction and method for long defects generating inclination along the perimeter of product section perpendicular to running direction, by using different wavelengths or switching on single sectors of illuminator at different times.

7. The method as claimed in claim 1, wherein high temperature product inspection is made possible by using illuminators and cameras operating at wavelengths at which irradiation of hot material is quite reduced (green-blue-ultraviolet), and wherein a possible background radiation due to incandescence of material is subtracted while processing.

8. An apparatus for identifying surface defects of a long product while it is subjected to working, comprising:
a plurality of illuminators, provided along the long product, each one projecting light according to a set angle with respect to line perpendicular to the lightened surface portion;
a plurality of detectors, provided about the long product, with relevant main axis inclined with respect to said line according to a set angle, and
a computerized unit for acquiring and processing said images,
wherein lighting groups, emitting white light or light dedicated to a set wavelength, are provided in such a way to lighten according to subsequent different angles regions of long product, and are possibly singularly piloted to realize sequences of lighting conditions, and in that computerized unit for acquisition and processing of said images, to provide useful indications for recognizing surface defects on the basis of shape or luminous intensity variations, uses comparison between images obtained under different lighting conditions of the product; and
wherein long defects, generating inclination along perimeter of product section perpendicular with respect to running direction are made evident using one or more than one cameras provided transversely with respect to the product, and one or more than one illuminators surrounding inspection section and that are comprised of different sectors, and wherein defects are individuated by making a comparison of images obtained in the same region of the product when the latter is lightened by different combination of illuminators sectors.

* * * * *